US 9,737,327 B2

(12) United States Patent
Kojima et al.

(10) Patent No.: US 9,737,327 B2
(45) Date of Patent: Aug. 22, 2017

(54) FLUID EJECTION DEVICE AND MEDICAL APPARATUS

(71) Applicant: SEIKO EPSON CORPORATION, Tokyo (JP)

(72) Inventors: Hideki Kojima, Matsumoto (JP); Hirokazu Sekino, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 293 days.

(21) Appl. No.: 14/227,374

(22) Filed: Mar. 27, 2014

(65) Prior Publication Data
US 2014/0296895 A1 Oct. 2, 2014

(30) Foreign Application Priority Data

Mar. 28, 2013 (JP) ................................. 2013-067718

(51) Int. Cl.
*A61B 17/3203* (2006.01)
*A61B 17/00* (2006.01)

(52) U.S. Cl.
CPC ...... *A61B 17/3203* (2013.01); *A61B 2017/00154* (2013.01); *A61B 2560/02* (2013.01)

(58) Field of Classification Search
CPC .......... A61B 17/3203; A61B 17/32037; A61B 2017/32032; A61B 17/32035; B05B 5/16; B05B 12/14; B26F 1/26; B26F 3/004; Y10T 83/0591
USPC .......................................................... 606/167
See application file for complete search history.

(56) References Cited

U.S. PATENT DOCUMENTS

| 6,589,229 | B1 | 7/2003 | Connelly et al. |
| 7,901,374 | B2 | 3/2011 | Seto et al. |
| 2010/0069937 | A1* | 3/2010 | Seto ................ A61B 17/32037 606/167 |
| 2011/0037795 | A1 | 2/2011 | Kojima et al. |
| 2011/0196305 | A1 | 8/2011 | Katoh |

FOREIGN PATENT DOCUMENTS

| EP | 2 022 419 A2 | 2/2009 |
| EP | 2 286 745 A2 | 2/2011 |
| JP | 06-277283 A | 4/1994 |

(Continued)

OTHER PUBLICATIONS

Extended European Search Report dated Jun. 23, 2014 as received in Application No. 14161974.2.

*Primary Examiner* — Jonathan Miles
*Assistant Examiner* — Mikail Mannan
(74) *Attorney, Agent, or Firm* — Maschoff Brennan

(57) ABSTRACT

A fluid ejection device which ejects a fluid includes: an ejection tube which ejects the fluid; a fluid chamber which communicates with the ejection tube; a piezoelectric element capable of changing a volume of the fluid chamber; a controller which controls a drive voltage applied to the piezoelectric element; and a fluid supplying unit which supplies the fluid to the fluid chamber at a predetermined flow rate. If a maximum frequency available to be set of the drive voltage is fmax [Hz] and an amount of change in the volume of the fluid chamber when a maximum value available to be set of the drive voltage is applied to the piezoelectric element to drive the piezoelectric element is V1 [ml], the fluid supplying unit supplies the fluid at the predetermined flow rate above V1×fmax [ml/s].

8 Claims, 6 Drawing Sheets

(56) References Cited

FOREIGN PATENT DOCUMENTS

| | | | |
|---|---|---|---|
| JP | 2002-126092 | A | 5/2002 |
| JP | 2003-071448 | A | 3/2003 |
| JP | 2003-180826 | A | 7/2003 |
| JP | 2003-180827 | A | 7/2003 |
| JP | 2003-520648 | A | 7/2003 |
| JP | 2004-081573 | A | 3/2004 |
| JP | 2004-309163 | A | 11/2004 |
| JP | 2005-168958 | A | 6/2005 |
| JP | 2005-192807 | A | 7/2005 |
| JP | 2006-136376 | A | 6/2006 |
| JP | 2008-82202 | A | 4/2008 |
| JP | 2008-188160 | A | 8/2008 |
| JP | 2009-055958 | A | 3/2009 |
| JP | 2009-078041 | A | 4/2009 |
| JP | 2011-036533 | A | 2/2011 |
| JP | 2011-143145 | A | 7/2011 |
| JP | 2011-160868 | A | 8/2011 |
| JP | 2011-177411 | A | 9/2011 |
| JP | 2012-035101 | A | 2/2012 |
| JP | 2013-047519 | A | 3/2013 |
| WO | 01/54753 | A2 | 8/2001 |

* cited by examiner

HOW PULSATING FLOW IS EJECTED

FLUID EJECTION DEVICE AND MEDICAL APPARATUS

This application claims the benefit of Japanese Patent Application No. 2013-67718, filed on Mar. 28, 2013. The content of the aforementioned application is incorporated herein by reference in its entirety.

BACKGROUND

1. Technical Field

The present invention relates to a fluid ejection device and a medical apparatus using the fluid ejection device.

2. Related Art

As a medical apparatus which ejects a fluid to a living tissue of a patient for treatment, for example, a device disclosed in JP-A-2008-82202 is known. In the fluid ejection device disclosed in JP-A-2008-82202, a piezoelectric element is driven to increase or decrease the volume of a fluid chamber, thus causing a pulsating flow (pulse flow) to be ejected from an ejection tube.

Since a fluid ejection device is used, for example, as a surgical knife, a stable sense of use is demanded of the fluid ejection device. There is also a demand that failure to eject a proper pulsating flow due to a shortage of a fluid supplied to the fluid ejection device should be restrained. Moreover, there is a demand that staying of a fluid at the affected part due to excess supply of the fluid to the fluid ejection device should be restrained.

Also, a reduction in size, a reduction in cost, resource saving, easier manufacturing, improvement in usability and the like are demanded of the traditional fluid ejection devices.

SUMMARY

An advantage of some aspects of the invention is to solve at least a part of the problems described above, and the invention can be implemented as the following aspects.

(1) An aspect of the invention provides a fluid ejection device which ejects a fluid. This fluid ejection device includes: an ejection tube which ejects the fluid; a fluid chamber which communicates with the ejection tube; a fluid supplying unit which supplies the fluid to the fluid chamber at a predetermined flow rate; a pulsation generator which causes the fluid in the fluid chamber to be ejected from the ejection tube; and a controller which controls operation of the pulsation generator to cause the fluid to be ejected periodically from the ejection tube. If a maximum frequency at which the control unit causes the fluid to be ejected is fmax [Hz], and an amount of change in volume of the fluid chamber when the control unit causes the pulsation generator to operate is V1 [ml], the fluid supplying unit supplies the fluid at the predetermined flow rate above V1×fmax [ml/s]. According to the fluid ejection device of this aspect, a shortage of the fluid in the fluid chamber when the pulsation generator is driven can be restrained, and the fluid is supplied at the predetermined flow rate. Therefore, the flow rate of the fluid ejected from the ejection tube is stable and a stable sense of use can be realized.

(2) In the fluid ejection device of the aspect described above, the fluid supplying unit may supply the fluid at the predetermined flow rate below V1×2.0×fmax [ml/s]. According to the fluid ejection device of this aspect, excess supply of the fluid to the fluid chamber can be restrained.

(3) In the fluid ejection device of the aspect described above, when the fluid in a volume V1 [ml] is ejected from the ejection tube by driving the pulsation generator once, if a volume of the fluid ejected from the ejection tube together with the fluid of the volume V1 [ml] by an inertial effect of the fluid is V2 [ml], the fluid supplying unit may supply the fluid at the predetermined flow rate equal to or above (V1+V2)×fmax [ml/s]. According to the fluid ejection device of this aspect, the fluid can be supplied to the fluid chamber at a proper flow rate in consideration of the inertial effect of the fluid.

(4) In the fluid ejection device of the aspect described above, the volume V2 may be V1×0.007. According to the fluid ejection device of this aspect, the fluid can be supplied to the fluid chamber at a proper flow rate in consideration of the inertial effect of the fluid.

(5) Another of the invention provides a medical apparatus using the fluid ejection device of the aspect described above. According to this aspect, a highly reliable medical apparatus can be provided.

Not all of the plural components provided in each of the above aspects of the invention are essential. In order to solve a part or all of the foregoing problems, or in order to achieve a part or all of the advantages described herein, apart of the plural components can be properly changed, deleted, replaced with another new component, or partly deleted in a limited context. Also, in order to solve a part or all of the foregoing problems, or in order to achieve a part or all of the advantages described herein, apart or all of the technical features included in one aspect of the invention can be combined with a part or all of the technical features of another aspect of the invention described above, to form a different aspect of the invention.

For example, an aspect of the invention can be realized as a device having one or more of the following five components: an ejection tube, a fluid chamber, a piezoelectric element, a controller, and a fluid supplying unit. That is, this device may or may not have an ejection tube. Similarly, the device may or may not have a fluid chamber. Also, the device may or may not have a piezoelectric element. The device may or may not have a controller. The device may or may not have a fluid supplying unit. The ejection tube may be formed, for example, as an ejection tube having an opening for ejecting the fluid. The fluid chamber may be formed, for example, as a fluid chamber which communicates with the ejection tube. The piezoelectric element may be formed, for example, as a piezoelectric element capable of changing the volume of the fluid chamber. The controller may be formed, for example, as a controller which controls a drive voltage applied to the piezoelectric element. The fluid supplying unit may be formed, for example, as a fluid supplying unit which supplies the fluid to the fluid chamber at a predetermined flow rate. Specifically, the fluid supplying unit may be formed as a fluid supplying unit which supplies the fluid at the predetermined flow rate above V1×fmax [ml/s], if the maximum frequency of the drive voltage is fmax [Hz] and the amount of change in the volume of the fluid chamber when the drive voltage of the maximum value is applied to the piezoelectric element to drive the piezoelectric element is V1 [ml]. Such a device can be realized, for example, as a fluid ejection device which ejects a fluid but can also be realized as another device but not only the fluid ejection device which ejects a fluid. According to such an aspect, at least one of the various problems such as a reduction in the size of the device, a reduction in cost, resource saving, easier manufacturing, and improvement in usability can be solved. A part of all of the technical features of each aspect of the foregoing fluid ejection device which ejects a fluid can be applied to this device.

The invention can also be realized in various other aspects than the device. For example, the invention can be realized in such aspects as a method for ejecting a fluid and a method for manufacturing a fluid ejection device.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments of the invention will be described, in order of an embodiment, an experiment example, and modifications.

A. First Embodiment

Figure 1:
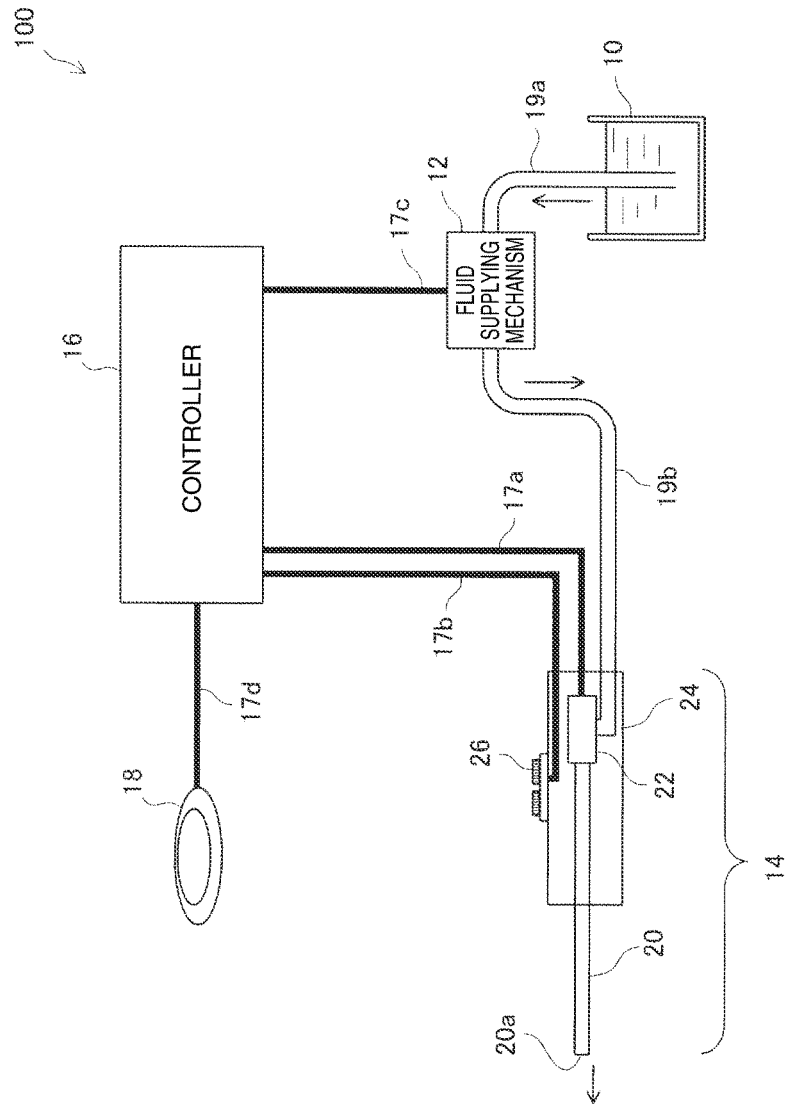
FIG. 1 is an explanatory view showing the configuration of a fluid ejection device as an embodiment of the invention.

FIG. 1 is an explanatory view showing the configuration of a fluid ejection device 100 as an embodiment of the invention. The fluid ejection device 100 of this embodiment is a medical apparatus used in a medical institution and has the function of a surgical knife which ejects a fluid to a living tissue of an affected part of a patient and thereby performs treatment such as incision or excision of the affect part.

The fluid ejection device 100 has a fluid container 10, a fluid supplying mechanism 12, a handpiece 14, a controller 16, and a foot switch 18. The fluid container 10 and the fluid supplying mechanism 12 are connected to each other by a connection tube 19a. The fluid supplying mechanism 12 and the handpiece 14 are connected to each other by a connection tube 19b. In this embodiment, the connection tubes 19a, 19b are made of a resin.

The fluid container 10 houses a physiological saline solution as a fluid to be supplied to the handpiece 14. However, the fluid container 10 may house another fluid that is harmless when ejected to a living tissue, for example, pure water, a drug solution or the like, instead of the physiological saline solution.

The fluid supplying mechanism 12 supplies the fluid housed in the fluid container 10 to the handpiece 14 via the connection tubes 19a, 19b. In this embodiment, a pump is used as the fluid supplying mechanism 12. Also, in this embodiment, as will be described later, the fluid supplying mechanism 12 supplies the fluid to the handpiece 14 at a predetermined flow rate.

The handpiece 14 is an instrument which the operator holds in the hand and operates. The handpiece 14 has a fluid ejection tube 20, a pulsation generator 22, a casing 24, and a condition switching unit 26. A fluid is supplied to the pulsation generator 22 via the connection tube 19b. When a drive voltage is applied to the pulsation generator 22 from the controller 16 via a voltage application cable 17a, the pulsation generator 22 generates pulsation in the supplied fluid. The fluid in which pulsation is generated is ejected at a high speed from an opening 20a at the forward end of the fluid ejection tube 20. The operator applies the fluid in which pulsation is generated and which is ejected from the handpiece 14, to a living tissue of an affected part of a patient, thereby performing treatment such as incision or excision of the affected part. Hereinafter, the fluid in which pulsation is generated is also called a pulsating flow or pulse flow.

The condition switching unit 26 is an operation unit for the operator to switch the magnitude and frequency of the drive voltage applied to the pulsation generator 22. In this embodiment, a dial-type selection unit is employed as the condition switching unit 26, and the operator selects a magnitude and frequency of the drive voltage used for treatment, from predefined magnitudes and frequencies of the drive voltage.

As the magnitude of the drive voltage is changed, the magnitude and strength of the pulsating flow is changed. As the frequency of the drive voltage is changed, the frequency of generation of the pulsating flow is changed. In this embodiment, the magnitude of the drive voltage that is available to be set and the frequency of the drive voltage that is available to be set are as follows.

Magnitude of drive voltage available to be set: 0 V to 100 V

Frequency of drive voltage available to be set: 100 Hz to 400 Hz

That it, in this embodiment, the maximum value available to be set Emax of the drive voltage is 100 V, and the maximum frequency available to be set fmax of the drive voltage is 400 Hz.

The controller 16 receives information about the magnitude and frequency of the drive voltage from the condition switching unit 26 via a control cable 17b and applies the drive voltage that satisfies the condition designated by the condition switching unit 26 to the pulsation generator 22 via the voltage application cable 17a. The controller 16 also controls the start and stop of the fluid supplying mechanism 12 via a control cable 17c.

The foot switch 18 is a switch which the operator operates with the foot and is connected to the controller 16 via a control cable 17d. As the operator turns on the foot switch 18, the controller 16 instructs the fluid supplying mechanism 12 to start supplying the fluid, and applies the drive voltage to the pulsation generator 22. Then, the fluid in which pulsation is generated is ejected at a high speed from the opening 20a at the forward end of the fluid ejection tube 20 of the handpiece 14.

Figure 2:
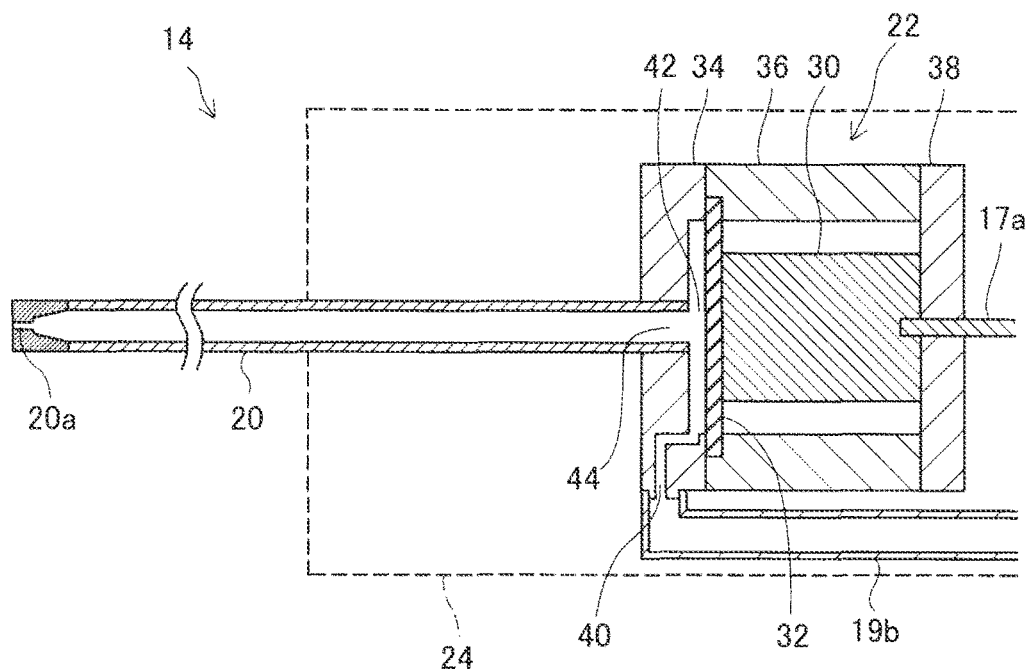
FIG. 2 is an enlarged cross-sectional view showing a part of the inner configuration of a handpiece.

FIG. 2 is an enlarged cross-sectional view showing a part of the inner configuration of the handpiece 14. Inside the casing 24 of the handpiece 14, the pulsation generator 22 which generates pulsation in the fluid supplied from the fluid supplying mechanism 12 is provided. The pulsation generator 22 has a piezoelectric element 30, a diaphragm 32, a first case 34, a second case 36, and a third case 38.

Inside the pulsation generator 22, an inlet channel 40, a fluid chamber 42, and an outlet channel 44 are formed as a channel through which the fluid supplied from the fluid supplying mechanism 12 passes. In this embodiment, the inlet channel 40 and the outlet channel 44 are formed in the first case 34. The fluid chamber 42 is formed between the first case 34 and the diaphragm 32. The connection tube 19b is connected to the inlet channel 40. The fluid ejection tube 20 is connected to the outlet channel 44.

The diaphragm 32 is a disc-shaped thin metal plate and an outer peripheral part thereof is held and fixed between the first case 34 and the second case 36.

The piezoelectric element 30 is an actuator which operates on receiving the drive voltage applied from the controller 16. The piezoelectric element 30 changes the volume of the fluid chamber 42 formed between the diaphragm 32 and the first case 34, thereby changing the pressure of the fluid in the fluid chamber 42. In this embodiment, the piezoelectric element 30 is a multilayer piezoelectric element, with one end thereof fixed to the diaphragm 32 and the other end thereof fixed to the third case 38.

When the drive voltage applied to the piezoelectric element 30 increases, the piezoelectric element 30 expands. The diaphragm 32 is pushed by the piezoelectric element 30 and flexes toward the fluid chamber 42. As the diaphragm 32 flexes toward the fluid chamber 42, the volume of the fluid chamber 42 decreases and the fluid in the fluid chamber 42 is extruded from the fluid chamber 42. In this embodiment, the inner diameter of the outlet channel 44 is greater than the inner diameter of the inlet channel 40. That is, since the inertance of the outlet channel 44 is smaller than the inertance of the inlet channel 40, the fluid in the fluid chamber 42 is extruded from the fluid chamber 42 through the outlet channel 44.

Meanwhile, when the drive voltage applied to the piezoelectric element 30 decreases, the piezoelectric element 30 contracts and the volume of the fluid chamber 42 increases. Thus, the fluid is supplied into the fluid chamber 42 from the inlet channel 40.

Since the drive voltage applied to the piezoelectric element 30 repeats on-state (maximum voltage) and off-state (0 V) at a high frequency (for example, 400 Hz), an increase and decrease in the volume of the fluid chamber 42 is repeated, thus generating pulsation in the fluid. The fluid extruded from the fluid chamber 42 is ejected from the nozzle 20a (opening 20a) at the forward end of the fluid ejection tube 20.

Figure 3:
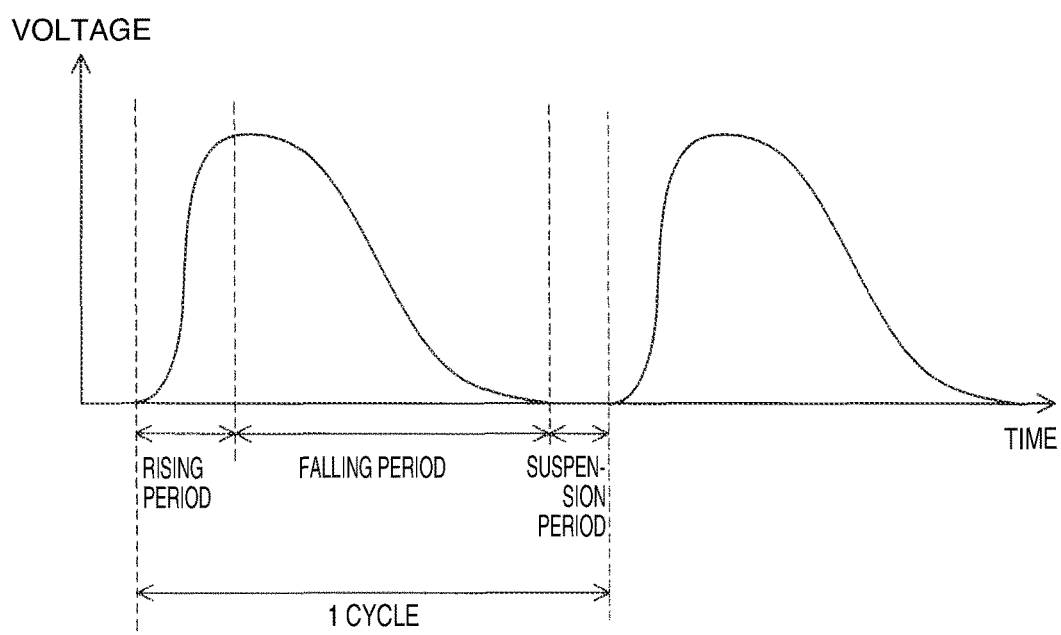
FIG. 3 is an explanatory view showing an example of the waveform of a drive voltage applied to a piezoelectric element.

FIG. 3 is an explanatory view showing an example of the waveform of the drive voltage applied to the piezoelectric element 30. In FIG. 3, the horizontal axis represents time and the vertical axis represents drive voltage. One cycle of the waveform of the drive voltage includes a rising period during which the voltage increases, a falling period during which the voltage decreases, and a suspension period during which no voltage is applied.

In this embodiment, the waveform in the rising period of the drive voltage is a SIN waveform ½-cycle waveform that is offset in the direction of positive voltage, with the phase thereof shifted by −90 degrees. The waveform in the falling period of the drive voltage is a SIN waveform ½-cycle waveform that is offset in the direction of positive voltage, with the phase thereof shifted by +90 degrees. The cycle of the SIN waveform in the falling period is greater than the cycle of the SIN waveform in the rising period.

In this embodiment, when the magnitude of the drive voltage is changed by the condition switching unit 26, the maximum value of the waveform shown in FIG. 3 is changed. Meanwhile, when the frequency of the drive voltage is changed by the condition switching unit 26, the waveforms in the rising period and the falling period are not changed and the length of the suspension period is changed.

Figure 4:
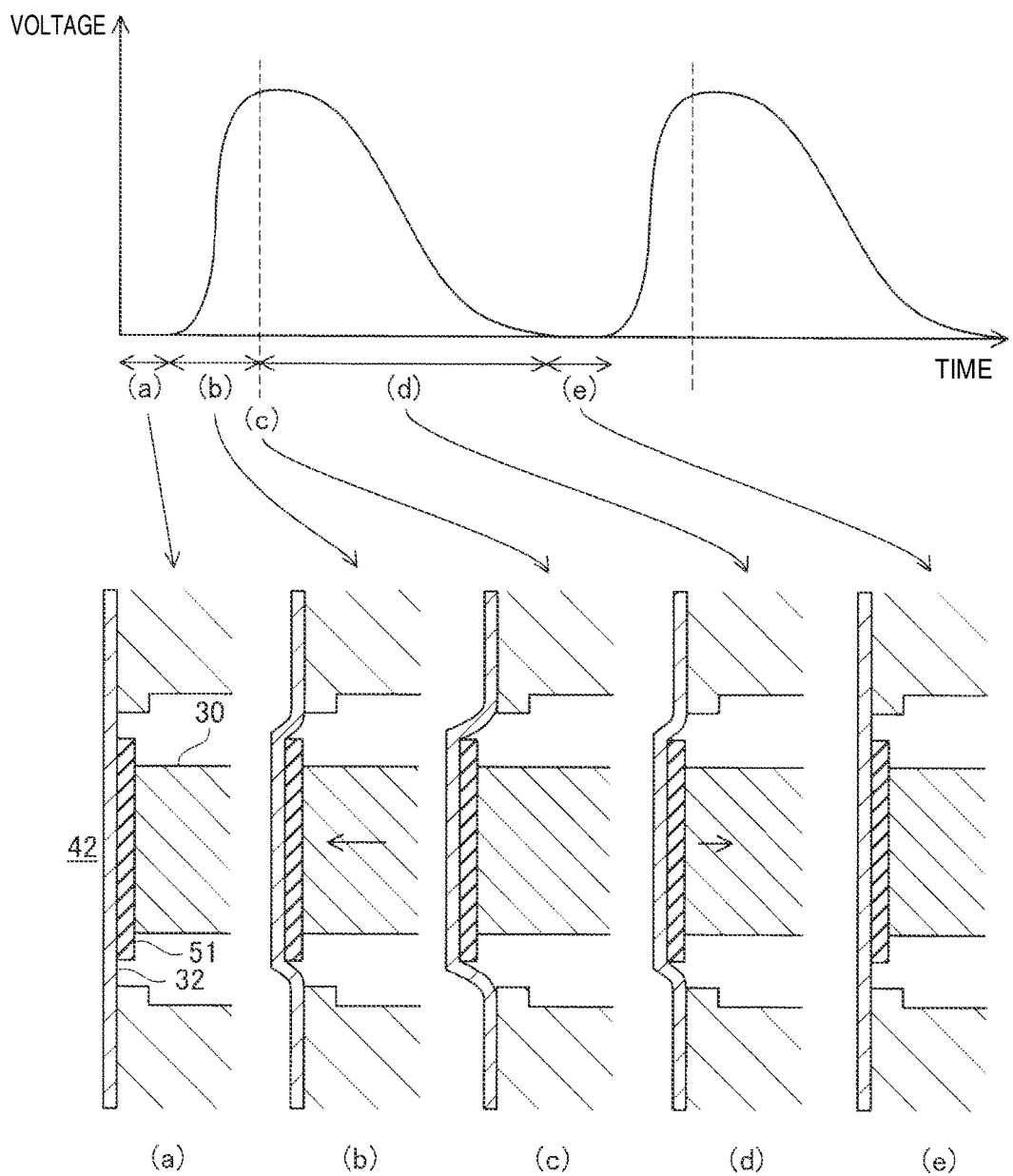
FIG. 4 is an explanatory view showing the correspondence between the waveform of a drive voltage and how a diaphragm is deformed.

FIG. 4 is an explanatory view showing the correspondence between the waveform of the drive voltage and how the diaphragm 32 is deformed. In FIG. 4, a reinforcing member 51 is provided between the piezoelectric element 30 and the diaphragm 32. During the suspension period (a), since no drive voltage is applied, the piezoelectric element 30 does not expand and the diaphragm 32 does not flex. During the rising period (b), since the drive voltage increases, the piezoelectric element 30 expands and the diaphragm 32 flexes toward the fluid chamber 42. The volume of the fluid chamber 42 decreases.

At the timing (c), since the drive voltage reaches the maximum, the length of the piezoelectric element 30 reaches the maximum and the volume of the fluid chamber 42 reaches the minimum. During the falling period (d), since the drive voltage decreases, the piezoelectric element 30 begins to restore the original size and the volume of the fluid chamber 42 begins to restore the original size. During the suspension period (e), since no drive voltage is applied, the piezoelectric element 30 restores the original size and the volume of the fluid chamber 42 restores the original size. As this series of operations shown by (a) to (e) is repeated, the fluid in the fluid chamber 42 is extruded to the fluid ejection tube 20.

Figure 5A:
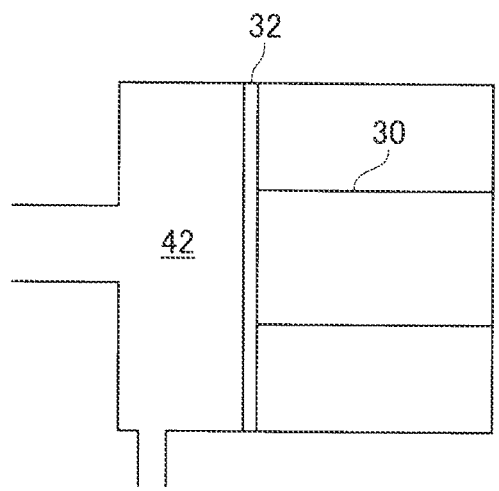
FIGS. 5A and 5B are explanatory views schematically showing a change in the volume of a fluid chamber.
Figure 5B:
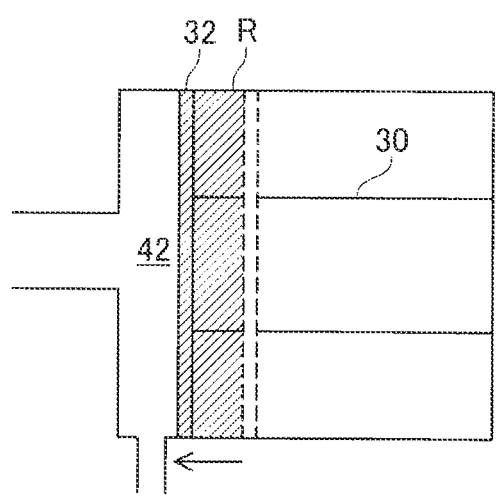

FIGS. 5A and 5B are explanatory views schematically showing a change in the volume of the fluid chamber 42. FIG. 5A shows the state where no drive voltage is applied to the piezoelectric element 30 and the volume of the fluid chamber 42 is at its maximum. FIG. 5B shows the state where the drive voltage applied to the piezoelectric element 30 is at its maximum and the volume of the fluid chamber 42 is at its minimum. A hatched area R in FIG. 5B represents the volume of the fluid chamber 42 changing during one cycle of the drive voltage. That is, the area R represents the volume of the fluid eliminated from the fluid chamber 42 during one cycle of the drive voltage. In this description, the volume of the fluid eliminated from the fluid chamber 42 during one cycle of the drive voltage is called an elimination volume. In the schematic views of FIGS. 5A and 5B, the elimination volume is found as the product of the cross-sectional area of the fluid chamber 42 and the length by which the piezoelectric element 30 is expanded.

In this embodiment, the elimination volume in the case where the piezoelectric element 30 is driven by a maximum drive voltage Emax available to be set by the condition switching unit 26 is defined as V1 [ml]. The maximum frequency available to be set by the condition switching unit 26 is defined as fmax [Hz]. Thus, when the piezoelectric element 30 is driven with the maximum drive voltage Emax and the maximum frequency fmax, the volume Vf [ml] of the fluid extruded from the fluid chamber 42 in one second is found as follows.

$$Vf = V1 \times fmax$$

However, in practice, a greater amount of the fluid than the elimination volume V1 is ejected from the fluid ejection tube 20 as a pulsating flow during one cycle of the drive voltage. Hereinafter, this phenomenon will be described.

Figure 6:
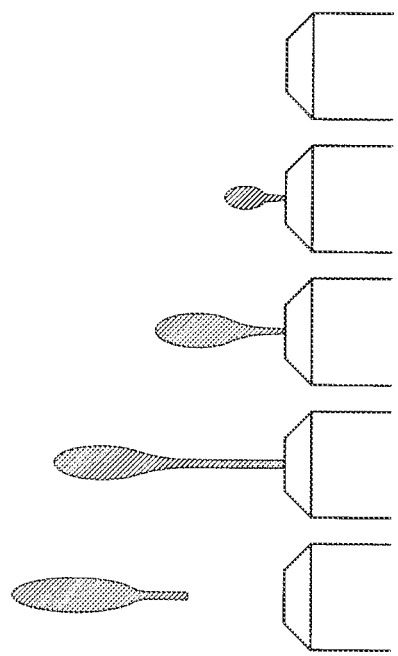
FIG. 6 is an explanatory view schematically showing how a fluid of a volume exceeding an elimination volume is ejected from a fluid ejection tube.

FIG. 6 is an explanatory view schematically showing how the fluid of an amount exceeding the elimination volume V1 is ejected from the fluid ejection tube 20. As shown in FIG. 6, as the piezoelectric element 30 is driven and a droplet-like pulsating flow is ejected from the fluid ejection tube 20, a streak-like droplet is ejected from the fluid ejection tube 20, continuing to the ejected droplet. This is because the inertial effect of the fluid causes the fluid in the fluid ejection tube 20 to be pulled by the ejected droplet. As a result, when the piezoelectric element 30 is driven with the maximum drive voltage Emax and the maximum frequency fmax, the fluid in the volume exceeding the elimination volume V1 is ejected from the fluid ejection tube 20 as a pulsating flow.

Therefore, in the case where the fluid supplying mechanism 12 supplies the fluid to the fluid chamber 42 at the flow rate of Vf [ml/s] and the piezoelectric element 30 is driven with the maximum drive voltage Emax and the maximum frequency fmax, a shortage of the fluid occurs and therefore a proper pulsating flow cannot be ejected.

Thus, in this embodiment, the fluid supplying mechanism 12 supplies the fluid at a predetermined flow rate above Vf [ml/s]. As a result, a shortage of the fluid can be restrained even in the case where the piezoelectric element 30 is driven with the maximum drive voltage Emax and the maximum frequency fmax.

Specifically, when the fluid in the volume of V1 [ml] is extruded from the fluid chamber 42 by driving the piezoelectric element 30 once, the volume of the fluid (streak-like droplet) ejected together with the fluid (droplet) in the volume of V1 [ml] by the inertial effect of the fluid is defined as V2 [ml]. In this case, the fluid supplying mechanism 12 of this embodiment supplies the fluid at a predetermined flow rate above (V1+V2)×fmax [ml/s]. Thus, the fluid can be supplied to the fluid chamber 42 at a proper flow rate in consideration of the fluid ejected by the inertial effect of the fluid, and therefore a shortage of the fluid can be restrained.

Moreover, in this embodiment, the fluid is supplied at a predetermined flow rate above Vf [ml/s], even if the magnitude and frequency of the drive voltage is changed by the condition switching unit 26. Therefore, since the predetermined flow rate of the fluid ejected from the fluid ejection tube 20 is maintained even if the drive voltage is low or even if the frequency of the drive voltage is low, the operator using the fluid ejection device 100 can experience a stable sense of use. If the drive voltage is changed to a lower value or to a lower frequency, the excess fluid that is supplied is discharged from the fluid ejection tube 20 as a continuous flow without pulsation.

It is confirmed that the volume V2 of the fluid (streak-like droplet) ejected by the inertial effect of the fluid is smaller than the elimination volume V1. Therefore, the volume of the fluid (V1+V2) ejected as a pulsating flow by driving the piezoelectric element 30 once is smaller than V1×2.0. Thus, the fluid supplying mechanism 12 of this embodiment supplies the fluid to the fluid chamber 42 at a predetermined flow rate below V1×2.0×fmax [ml/s]. Therefore, according to this embodiment, since excess supply of the fluid to the fluid chamber 42 can be restrained, excess discharge of a continuous flow without pulsation from the fluid ejection tube 20 can be restrained. As a result, the amount of the fluid used can be reduced and the amount of the fluid remaining on a treatment target can be reduced. Thus, a good operating field can be secured.

In this way, according to this embodiment, since the fluid is supplied at a predetermined flow rate above Vf [ml/s], even in the case where the piezoelectric element 30 is driven with the maximum drive voltage Emax and the maximum frequency fmax, a shortage of the fluid in the fluid chamber 42 can be restrained and the operator using the fluid ejection device 100 can experience a stable sense of use.

In the actual fluid supplying mechanism 12, even in the case of supplying the fluid at a "predetermined" flow rate, it may be difficult to maintain the predetermined flow rate strictly and a variance of ±10% may occur. Therefore, the term "predetermined" used herein includes cases where a variance of ±10% occurs. Even in the case where the fluid supplying mechanism 12 is a roller pump, plunger pump or the like and has an instantaneous variance in the flow rate, the effect of the invention is hardly impaired as long as the average flow rate in a macroscopic time cycle is a predetermined flow rate.

B. Experiment Example

In this experiment example, a pulsating flow ejected from the fluid ejection tube 20 is observed while the supply flow rate of the fluid by the fluid supplying mechanism 12 is changed. Thus, a proper supply flow rate of the fluid is found. Then, how large the volume V2 of the fluid (streak-like droplet) ejected by the inertial effect of the fluid is, relative to the elimination volume V1, is examined. The state where the supply flow rate of the fluid is proper refers to the state where a proper pulsating flow is ejected and an unnecessary continuous flow does not occur between pulsating flows. The reason why a continuous flow is not necessary is because a continuous flow is extruded simply by the pressure from the fluid supplying mechanism 12 and therefore hardly contributes to incision, excision or the like of an affected part. Moreover, the occurrence of a continuous flow causes an increase of the fluid remaining at the affected part and therefore narrows the operating field.

The conditions in this experiment example are as follows.

Maximum drive voltage Emax: 100 V

Maximum frequency fmax: 400 Hz

Maximum displacement of piezoelectric element when maximum drive voltage Emax is applied: 10 μm Diameter of fluid chamber: 6 mm Cross-sectional area of fluid chamber: $2.83 \times 10^{-5}$ m$^2$ According to the above conditions, the elimination volume V1 is found as follows.

Elimination volume V1: $2.83 \times 10^{-10}$ m$^3$

The elimination volume per minute is expressed by the following equation (1).

$$V1 \times f\text{max} \times 60 = 6.79 \text{ ml/minute} \quad (1)$$

Figure 7:
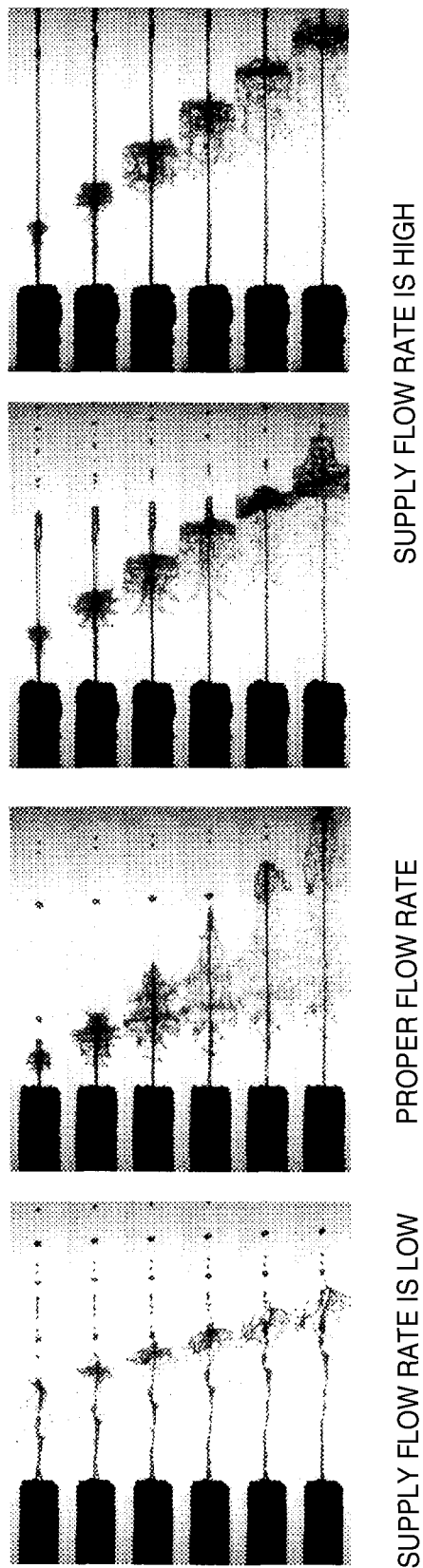
FIG. 7 is an explanatory view showing sequence photographs of the moment of ejection of a pulsating flow.

FIG. 7 is an explanatory view showing sequence photographs of the moments of ejection of a pulsating flow. In FIG. 7, the case where the supply flow rate of the fluid is low, the case where the supply flow rate is proper, and the case where the supply flow rate is high are shown. As shown in FIG. 7, in the case where the supply flow rate of the fluid is low, the fluid in the fluid ejection tube 20 is extruded before the fluid ejection tube 20 is filled with the fluid. Therefore, the ejected pulsating flow is weak. Meanwhile, in the case where the supply flow rate of the fluid is high, a continuous flow is generated immediately before a pulsating flow is generated, and a high-speed pulsating flow is generated after the continuous flow. Since the fluid in the fluid ejection tube 20 is extruded instantaneously, the speed of the pulsating flow is higher than the speed of the continuous flow.

In the case where the supply flow rate of the fluid is proper, no unnecessary continuous flow is generated and a pulsating flow is generated intermittently. Specifically, after the fluid ejection tube 20 is filled with the fluid, the fluid in the fluid ejection tube 20 is extruded instantaneously, generating a pulsating flow with great strength. While the fluid ejection tube 20 is filled with the fluid again, no unnecessary continuous flow is generated. After the fluid ejection tube 20 is filled with the fluid, a pulsating flow is generated again.

As a result of the above experiment, the proper supply flow rate of the fluid is found to be 6.84 ml/minute. Therefore, the following equation (2) holds.

$$(V1+V2) \times f\text{max} \times 60 = 6.84 \text{ ml/minute} \quad (2)$$

Subtracting the equation (1) from the equation (2) results in the following equation (3).

$$V2 \times f\text{max} \times 60 = 0.05 \text{ ml/minute} \quad (3)$$

Based on the equations (1) and (3), the relation between V2 and V1 can be derived as expressed by the following equation (4).

$$V2 = V1 \times 0.007 \quad (4)$$

According to the above calculations, under the conditions of this experiment example, the volume V2 of the fluid (streak-like droplet) ejected by the inertial effect of the fluid is approximately 0.007 times the elimination volume V1. However, the ratio of V1 to V2 varies depending on the configuration of the fluid ejection device 100 and the nature of the fluid. Therefore, it is preferable to set a proper ratio of V1 to V2 according to the configuration of the fluid ejection device 100 and the nature of the fluid.

C. Modifications

The invention is not limited to the above embodiment and experiment example and can be carried out in various forms without departing from the scope of the invention. For example, the following modifications can be made.

Modification 1

In the embodiment, the fluid ejection device 100 is used as a medical apparatus. However, as a modification, the fluid ejection device 100 may be used as another apparatus than the medical apparatus. For example, the fluid ejection device 100 may be used as a cleaning device which ejects a fluid to a target object and thus removes stains from the target object, or a drawing device which draws letters and pictures with the ejected fluid.

Modification 2

In the embodiment, a liquid is used as a fluid ejected from the fluid ejection device 100. However, as a modification, a gas may be used as a fluid ejected from the fluid ejection device 100.

Modification 3

In the embodiment, the magnitude of the drive voltage available to be set ranges from 0 V to 100 V and the frequency of the drive voltage available to be set ranges from 100 Hz to 400 Hz. However, as a modification, the range of the magnitude of the drive voltage available to be set and the range of the frequency of the drive voltage available to be set may be different from the above ranges. For example, the frequency of the drive voltage available to be set may range from 100 Hz to 1000 Hz.

Modification 4

In the embodiment, the elimination volume V1 is found as the product of the cross-sectional area of the fluid chamber 42 and the maximum displacement of the piezoelectric element 30. However, strictly speaking, it is preferable that the elimination volume V1 is equal to the actual amount of change in the volume of the fluid chamber 42. Therefore, for example, when the piezoelectric element 30 expands to raise the internal pressure in the fluid chamber 42, it is preferable to consider the amount of contraction due to the elastic deformation of the piezoelectric element 30 under the pressure. It is also preferable to consider the shape of the diaphragm 32 when deformed. If the piezoelectric constant of the piezoelectric element 30 is known, the displacement of the piezoelectric element 30 may be found based on the piezoelectric constant and the drive voltage.

Modification 5

In the embodiment, the configuration in which the volume of the fluid chamber 42 decreases as the drive voltage applied to the piezoelectric element 30 increases is employed. However, as a modification, a configuration in which the volume of the fluid chamber 42 increases as the drive voltage applied to the piezoelectric element 30 increases may be employed.

Modification 6

In the embodiment, the condition switching unit 26 is provided on the handpiece 14. However, as a modification, the condition switching unit 26 may be provided at another position than on the handpiece 14. For example, the condition switching unit 26 may be provided in the controller 16.

Modification 7

In the embodiment, a piezoelectric element is used as the pulsation generator 22. However, as a modification 7, an air bubble generator may be used as the pulsation generator. As the air bubble generator, for example, a heater, laser beam casting unit or the like may be used. As the air bubble generator, any unit that heats the fluid in the fluid chamber and thus generates air bubbles so that the fluid in the fluid chamber is ejected by expansion of the generated air bubbles can be used.

In such a case, the controller controls the air bubble generator to generate air bubbles periodically. If the maximum frequency at which the controller causes the air bubble generator to generate air bubbles is fmax [Hz] and the amount of change in the volume of the fluid chamber in the case where a maximum amount of air bubbles is generated by the air bubble generator is V1 [ml], the fluid supplying unit may supply the fluid at the predetermined flow rate above V1×fmax [ml/s].

Modification 8

A part of the functions realized by software in the embodiment may be realized by hardware. Alternatively, a part of the functions realized by hardware may be realized by software.

The invention is not limited to the above embodiment, example and modifications and can be realized in various configurations without departing from the scope of the invention. For example, the technical features in the embodiment, example and modifications corresponding to the technical features in the respective embodiments described in the summary of the invention can be suitably replaced or combined in order to solve a part or all of the foregoing problems or in order to achieve a part or all of the foregoing advantages. Also, the technical features can be suitably deleted unless these features are described as essential herein.

What is claimed is:

1. A fluid ejection device which ejects a fluid, comprising:
an ejection tube which ejects the fluid;
a fluid chamber which communicates with the ejection tube;
a fluid supplying unit which supplies the fluid to the fluid chamber at a predetermined flow rate;

a pulsation generator which causes the fluid in the fluid chamber to be ejected from the ejection tube; and a controller which controls operation of the pulsation generator to cause the fluid to be ejected periodically from the ejection tube;

wherein a maximum frequency at which the controller causes the fluid to be ejected is fmax [Hz], and an amount of change in volume of the fluid chamber when the controller causes the pulsation generator to operate by applying a maximum value of a drive voltage is V1 [ml], the fluid supplying unit is configured to supply the fluid at the predetermined flow rate above V1×fmax [ml/s], such that the predetermined flow rate is maintained even when the drive voltage is lower than the maximum value or when the frequency of the drive voltage is lower than the maximum frequency.

2. The fluid ejection device according to claim 1, wherein the fluid supplying unit supplies the fluid at the predetermined flow rate below V1×2.0×fmax [ml/s].

3. The fluid ejection device according to claim 1, wherein when the fluid in a volume V1 [ml] is ejected from the ejection tube by driving the pulsation generator once, if a volume of the fluid ejected from the ejection tube together with the fluid of the volume V1 [ml] by an inertial effect of the fluid is V2 [ml], the fluid supplying unit supplies the fluid at the predetermined flow rate equal to or above (V1+V2)×fmax [ml/s].

4. The fluid ejection device according to claim 3, wherein the volume V2 is V1×0.007.

5. A medical apparatus comprising the fluid ejection device according to claim 1.

6. A medical apparatus comprising the fluid ejection device according to claim 2.

7. A medical apparatus comprising the fluid ejection device according to claim 3.

8. A medical apparatus comprising fluid ejection device according to claim 4.

* * * * *